United States Patent [19]   [11]  4,332,960
Trösken et al.   [45]  Jun. 1, 1982

[54] HERBICIDAL COMPOSITIONS

[75] Inventors: Jürgen Trösken, Walldorf; Gerhard Hörlein, Frankfurt am Main; Ernst-Friedrich Schulze, Hofheim; Peter Langelüddeke, Diedenbergen, all of Fed. Rep. of Germany

[73] Assignee: Hoechst Aktiengesellschaft, Frankfurt am Main, Fed. Rep. of Germany

[21] Appl. No.: 594,031

[22] Filed: Jul. 8, 1975

[30] Foreign Application Priority Data

Jul. 10, 1974 [DE] Fed. Rep. of Germany ....... 2433067

[51] Int. Cl.³ ............................................. C07C 69/76
[52] U.S. Cl. ....................................... 560/62; 71/108; 71/116; 71/118; 71/100; 562/472; 260/501.1

[58] Field of Search .............. 260/473 G; 71/108, 116

Primary Examiner—Paul J. Killos
Attorney, Agent, or Firm—Curtis, Morris & Safford

[57] ABSTRACT

Compounds of the formula

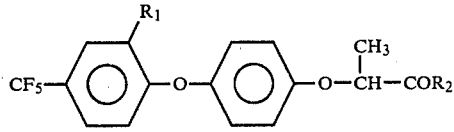

where $R_1$ is H or Hal and $R_2$ is a variety of functional groups among which is hydroxy, alkoxy and (substituted) amino, are valuable grass herbicides.

10 Claims, No Drawings

HERBICIDAL COMPOSITIONS

The present invention relates to herbicidal compositions.

German Offenlegungsschrift No. 2,223,894 describes 4-phenoxy-phenoxy-alkane-carboxylic acids and their derivatives and discloses the herbicidal action of the said compounds. Compounds of this type are also the object of German Offenlegungsschriften No. 1,668,896 and 1,136,828.

Up to now, 4-phenoxy-phenoxy-alkane-carboxylic acids containing trifluoromethyl groups have not been described.

It has now been found that such (4-trifluoromethyl-phenoxy)-phenoxy-propionic acids and their functional derivatives have a very good selective herbicidal effect against weed grasses in crop plants.

The present invention therefore provides compounds of the formula I

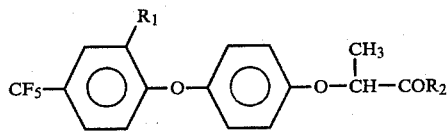

in which
R$_1$ is hydrogen or halogen,
R$_2$ is hydroxy, (C$_1$-C$_6$)alkoxy, cyclohexyloxy, phenyloxy, phenylthio, hydrazino, amino, (C$_1$-C$_4$)—alkylamino, di(C$_1$-C$_4$) alkylamino, phenylamino, halophenylamino, trifluoromethylphenylamino, or the group —O-cat wherein "cat" is the cation of an inorganic or organic base.

Preferred radicals R$_2$ are hydroxy, (C$_1$-C$_6$)alkoxy and —O-cat wherein cat is, for example, Na$^+$, K$^+$, NH$_4^+$, ½Ca$^{2+}$, or the cation of an organic base, such as trimethylamine, triethylamine, pyridine, or dimethylaniline. R$_1$ preferably represents hydrogen.

The compounds of formula I are prepared by reacting
(a) 4-phenoxyphenols of the formula II

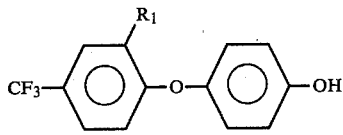

with propionic acid derivatives of formula III

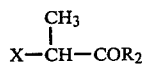

in which X is halogen or a sulfonic acid ester group, or
(b) 4-halogeno-diphenyl ethers of the formula IV

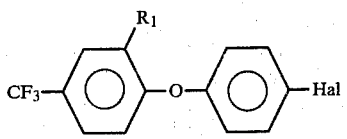

with lactic acid or its functional derivatives of the formula V

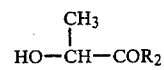

and optionally transferring the compounds of formula I into other functional derivatives of formula I by esterification, saponification, salt formation, ester interchange, or amidation.

In formulae III and IV the term "halogen" preferably stands for chlorine or bromine; preferred halogen-propionic acids, are therefore, α-bromo- and α-chloropropionic acid. Suitable sulfonic ester derivatives of formula III are primarily, those of methanesulfonic acid (mesylates), of p-toluenesulfonic acid (tosylates), of benzenesulfonic acid, and of p-bromobenzenesulfonic acid.

The reaction according to (a) is preferably carried out in an organic solvent, for example a ketone such as acetone or diethylketone, a carboxylic acid amide such as dimethyl formamide, a sulfoxide such a dimethyl sulfoxide, or an aromatic hydrocarbon such as benzene or toluene, and in the presence of an alkaline compound to bind the hydrogen halide or sulfonic acid set free in the course of the reaction, for example in the presence of potassium carbonate of a tertiary organic base such as triethylamine.

When the reaction is terminated the reaction product is separated from the hydrohalic or sulfonic acid salts formed by filtration or dilution with water and then isolated, after removal of the organic solvent.

The derivatives obtained can be purified by usual methods, for example by distillation or recrystallization from organic solvents, optionally in admixture with water.

The reaction according to (b) is carried out under the known conditions of the Ullmann phenyl ether synthesis.

The various functional derivatives of formula I can be transferred into one another in known manner. For example, the carboxylic acid esters can be saponified with alkali, preferably by using aqueous bases in the presence of alcohols, and heating. The alcaline solution is then acidified whereby the free acid separates in the form of crystals or as an oil.

When free halogeno-propionic acids are reacted with the phenoxyphenols the carboxyl group can subsequently be esterified in usual manner. For this purpose, catalytic amounts of an acid are used, for example sulfuric acid, toluenesulfonic acid or hydrochloric acid. Other acid catalyst, for example Lewis acids such as boron trifluoride or an acid ion exchanger, may also be used.

Suitable alcohols for the esterification are aliphatic straight chain or branched alcohols having from 1 to 6 carbon atoms, or cyclohexanol.

For the esterification also the readily accessible acid chlorides can be used. These are obtainable for example by reacting the carboxylic acids of formula I with thionyl chloride and form the corresponding esters by reaction with the aforesaid alcohols.

Further derivatives of formula I are obtained by reacting the acid chlorides with amines or anilines. The corresponding amides can be obtained by reacting the esters with amines.

The starting compounds of formula II can be obtained by reacting p-trifluorohalogenobenzenes of the formula VII

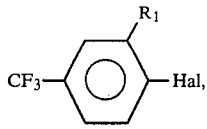

VII in which Hal preferably is chlorine or bromine, in polar solvents at temperatures of 120° to 200° C., with hydroquinone derivatives of the formula VIII

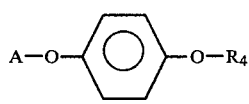

VIII in which A is a monovalent cation, preferably Na or K, and $R_4$ has the same meaning as A or represents hydrogen or a protective group for the second hydroxyl group of hydroquinone, for example an alkyl and preferably a $(C_1-C_4)$alkyl group, particularly methyl, or benzyl; the protective group $R_4$ is then split off if necessary.

The compounds of the invention are closely related chemically to the known phenoxy fatty acids, for example (2,4-dichlorophenoxy)-acetic acid and (2,4-dichloro-phenoxy)-propionic acid, but they are fundamentally different from the latter as regards their herbicidal activity. While the known herbicides control only dicotyledonous weeds, the invention compounds are effective exclusively against monocotyledonous weeds (weed grasses). Both in pre- and post-emergence application they destroy weed grasses in very low concentrations, while even considerable overdoses do no or only little harm to broad leaved plants. The effective of the novel compounds is particularly pronounced against perennial weed grasses such as couch grass (*Agropyron repens*) and Bermuda grass (*Cynodon dactylon*), which are notoriously difficult to control in crop plants with known herbicides. Surprisingly the novel compounds can also be used in rice (a grass like crop plant) to combat weed grasses. Moreover, weed grasses can be efficiently controlled in dicotyledonous crop plants. for example in sugar beet, leguminosae, cotton, vegetables and others.

Owing to this special activity against weed grasses, such as foxtail grass, wild oat, chickweed, foxtail millet, the novel compounds are superior to known herbicides in cultures strongly infested with weed grasses. A special advantage resides in the fact that the compositions of the invention can be applied both pre- and post-emergent, which is not possible with known selective weed grass herbicides. Triallate (N,N-diisopropyl-thiol-2,3,3-trichloro-allyl carbamate), Nitralin (N,N-dipropyl-2,6-dinitro-4-methylsulfonyl aniline), TCA (sodium trichloroacetate), for example, can only be used pre-emergent, while Chlorphenpropmethyl (2-Cl-3-(4'-chlorophenyl)-propionic acid methyl ester) can be used only post-emergent. A further advantage of the compositions of the invention is that they control a relatively great number of weed grasses, whereas widely used known products, for example the aforesaid herbicides, are effective only against a few types of weed grasses. Finally the amounts necessary for complete destruction of weed grasses are in many cases lower than the amounts required of the aforesaid known herbicides.

The compositions according to the invention contain the active ingredients of formula I generally in amount of from 2 to 95% by weight. They can be used in the form of wettable powders, emulsifiable concentrates, sprayable solutions, dusts, or granules, in admixture with the conventional inert components.

Wettable powders are preparations that can be uniformly dispersed in water and contain, besides the active ingredient, a diluent or an inert substance, a wetting agent, for example polyoxethylated alkylphenols, polyoxethylated oleyl- or stearyl-amines, alkyl- or alkylphenyl sulfonates, and dispersing agents, for example the sodium salt of lignin-sulfonic acid, of 2,2'-dinaphthylmethane-6,6'-disulfonic acid, of dibutylsulfonic acid or sodium oleylmethyltauride.

Emulsion concentrates are obtained by dissolving the active ingredient in an organic solvent, for example butanol, cyclohexanone, dimethylformamide, xylene, or aromatic hydrocarbons having a higher boiling point. To obtain suspensions or emulsions in water having good properties, wetting agents as specified above are also added.

Dusting powders are obtained by grinding the active ingredient with finely divided, solid substances, for example talc, natural clays such as kaolin, bentonite, pyrophillite, or diatomaceous earths.

Spraying solutions commercially available as aerosol sprays contain the active ingredient dissolved in an organic solvent, and in addition thereto a propellant, for example a mixture of fluorochlorohydrocarbons.

Granules can be produced by atomizing the active ingredient on to an adsorptive, granulated inert material, or by applying concentrates of the active ingredient to the surface of a support, for example sand, kaolinite or a granulated inert material, with the aid of an adhesive, for example polyvinyl alcohol, the sodium salt of polyacrylic acid, or mineral oils. Alternatively, suitable active ingredients may be made into granules, if desired in admixture with fertilizers, in the manner commonly used for the manufacture of granulated fertilizers.

The commercial herbicidal preparations contain varying concentrations of the active ingredients. In wettable powders the concentration of active ingredient varies, for example, from about 10 to 95%, the remainder being the above formulation additives. Emulsion concentrates contain about 10 to 80% of active ingredient, while dusting powders mostly contain 5 to 20% of active ingredient and sprayable solutions about 2 to 20%. In the case of granules, the content of active ingredient partially depends on whether the active ingredient is liquid or solid and on the type of granulation auxiliary or filler used.

For application the commercial concentrates are optionally diluted in usual manner, the wettable powder or emulsifiable concentrate for example with water. Dusts and granulated formulations as well as sprayable solutions are not diluted further with an inert substance before their application. The amount applied varies with the external conditions, such as temperature, humidity and the like. In general, about 0.1 to 10.0 kilograms and preferably 0.3 to 2.5 kilograms of active ingredient per hectare are used.

The herbicides according to the present invention may be combined with other herbicides and soil insecticides.

Known herbicides suitable for combination with the novel compounds of the invention are, for example, the following compounds listed by their common or chemical names:

| | |
|---|---|
| urea derivatives | linuron, chloroxuron, monolinuron, fluometuron, diuron; |
| triazine derivatives | simazin, atrazin, ametryne, prometryne, desmetryne, methoprotryne; |
| uracil derivatives | lenacil, bromacil; |
| pyrazone derivatives | 1-phenyl-4-amino-5-chloro-pyridazone-(6); |
| growth-promoting preparations | 2,4-dichlorophenoxy-acetic acid, 4-chloro-2-methylphenoxy-acetic acid, 2,4,5-trichlorophenoxyacetic acid, 4-chloro-2-methylphenoxy-butyric acid, 2,3,6-trichloro-benzoic acid; |
| carbamic acid derivatives | barban, phenmedipham, triallate, diallate, vernolate, and 2-chloro-allyl-N,N-diethyl-dithiocarbamate, swep; |
| dinitrophenol derivatives | dinitro-orthocresol, dinoseb, dinosebacetate |
| chlorinated aliphatic acids | trichloroacetic acid, dalapon |
| amides | diphenamide, N,N-diallyl-chloro-acetamide |
| dipyridilium compounds | paraquat, diquat, morfamquat |
| anilides | N-(3,4-dichlorophenyl)-methacrylamide, propanil, solan, monalide, 2-chloro-2',6'-diethyl-N-(methoxymethyl)-acetanilide, propachlor |
| nitriles | dichlobenil, ioxynil |
| other preparations | flurenol, 3,4-dichloropropion-anilide, trifluralin, bensulide, monosodium methyl arsonate, 4-trifluoro-methyl-2,4-dinitrodiphenyl ether. |

When the active ingredients according to the invention are mixed with fertilizers, preparations are obtained which simultaneously have a fertilizing and a herbicidal effect.

Formulation Examples

EXAMPLE A

A wettable powder which is readily dispersible in water can be obtained by mixing
  25 parts be weight of α-[4-(4'-trifluoromethyl-phenoxy)-phenoxy]-propionic acid as active ingredient
  64 parts by weight of kaolin-containing quartz as inert substance
  10 parts by weight of the potassium salt of lignin-sulfonic acid
  1 part by weight of sodium oleylmethyl tauride as wetting and dispersing agent,
and grinding the mixture obtained in a disk attrition mill.

EXAMPLE B

A dusting powder having good herbicidal properties can be obtained by mixing
  10 parts by weight of α-[4-(4'-trifluoromethyl-phenoxy)-phenoxy]-propionic acid as active ingredient
  90 parts by weight of talcum as inert substance
and grinding the mixture obtained in a cross-beater mill.

EXAMPLE C

An emulsifiable concentrate consists of
  15 parts by weight of α-[4-(2'-chloro-4'-trifluoromethyl-phenoxy)-phenoxy]-propionic acid
  75 parts by weight of cyclohexanone as solvent and
  10 parts by weight of nonyl phenol polyoxyethylene (10 ethoxy units) as emulsifier.

The following examples illustrate the invention.

EXAMPLES OF PREPARATION

EXAMPLE 1

α-[4-(4'-trifluoromethyl-phenoxy)-phenoxy]-propionic acid ethyl ester 25.4 g (0.1 mole) 4-trifluoromethyl-4'-hydroxy-diphenyl ether were dissolved in 100 ml dimethyl formamide, 20 g (0.145 mole) K$_2$CO$_3$ and 19 g (0.124 mole) α-bromopropionic acid ethyl ester were added and the mixture was heated for 3 hours to 100° C. while stirring. The reaction mixture was poured into 400 ml of water and the organic layer was separated. The aqueous phase was extracted with methylene chloride, the combined organic layers were dried and concentrated. 31.5 g (89% of theory) of α-[4-(4'-trifluoromethyl-phenoxy)-phenoxy]-propionic acid ethyl ester melting at 45°–48° C. were obtained.

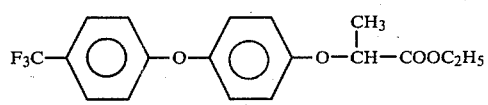

EXAMPLE 2

α-[4-(4'-trifluoromethyl-phenoxy)-phenoxy]-propionic acid 81 g (0.23 mole) of the ester obtained in the preceding example were heated while stirring together with 300 ml of 2 N NaOH until a clear solution had formed. In a rotary evaporator the solution was concentrated to two third of its volume and acidified with concentrated hydrochloric acid. The precipitate formed was filtered off with suction and washed with water. After recrystallization from toluene/petroleum ether 68 g (91% of theory) of α-[4-(4'-trifluoromethyl-phenoxy)-phenoxy]-propionic acid melting at 140°–143° C. were obtained.

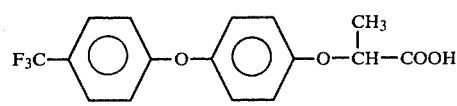

EXAMPLE 3

α-[4-(2'-chloro-4'-trifluoromethyl-phenoxy)-phenoxy]-propionic acid n-hexyl ester 20 g (0.145 mole) of pulverulent potassium carbonate and 25 g (0.11 mole) α-bromopropionic acid n-hexyl ester were added to a solution of 28.9 g (0.1 mole) of 2-chloro-4'-hydroxy-4-trifluoromethyl-diphenyl ether in 100 ml dimethyl formamide, and the mixture was heated for 3 hours to 100° C. The mixture was poured on water, the organic phase was separated, extracted with ether, the organic solutions were dried and distilled. 36.6 g (89% of theory) α-[4-(2'-chloro-4'-trifluoromethyl-phenoxy)-phenoxy]-propionic acid n-hexyl ester were obtained in the form of an oil boiling at 194° C. under 0.002 mm Hg.

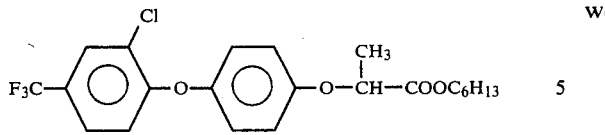

EXAMPLE 4

α-[4-(4'-trifluoromethyl-phenoxy)-phenoxy]-propionic acid methylamide 20 g (0.056 mole) of the ester as obtained in Example 1 were dissolved in 100 ml methanol, 20 ml 40% aqueous methylamine solution were added and the mixture was stirred until the precipitate formed had dissolved again. The mixture was allowed to stand for 6 hours, whereupon the reaction product was precipitated with water and recrystallized from methanol/water. 16.9 g (86% of theory) of α-[4-(4'-trifluoromethyl-phenxoy)-phenoxy]-propionic acid methyl amide melting at 129°-132° C. were obtained.

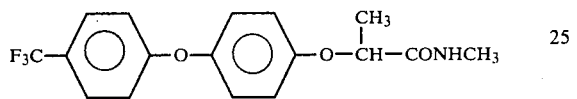

The following compounds of formula I were prepared in analogous manner:

TABLE

| Example No. | R₁ | R₂ | b.p./m.p. | |
|---|---|---|---|---|
| 5 | 4-CF₃ | H | OCH₃ | b.p.·0.045 142° C. |
| 6 | 4-CF₃ | H | OC₃H₇(n) | m.p. 39-40° C. |
| 7 | 4-CF₃ | H | OC₃H₇(i) | m.p. 36-38° C. |
| 8 | 4-CF₃ | H | OC₄H₉(n) | m.p. 36-38° C. |
| 9 | 4-CF₃ | H | OC₄H₉(i) | m.p. 55-57° C. |
| 10 | 4-CF₃ | H | OC₆H₁₃(n) | b.p.·0.05 178° C. |
| 11 | 4-CF₃ | H | O⊖ Na⊕ | — |
| 12 | 4-CF₃ | H | O⊖ NH(C₂H₅)₂⊕ | — |
| 13 | 4-CF₃ | 2-Cl | OH | m.p. 73-77° C. |
| 14 | 4-CF₃ | 2-Cl | OCH₃ | b.p.·0.05 155° C. |
| 15 | 4-CF₃ | 2-Cl | OC₂H₅ | b.p.·0.04 162° C. |
| 16 | 4-CF₃ | 2-Cl | OC₃H₇(n) | b.p.·0.2 162° C. |
| 17 | 4-CF₃ | 2-Cl | OC₃H₇(i) | b.p.·0.04 142° C. |
| 18 | 4-CF₃ | 2-Cl | OC₄H₉(n) | b.p.·0.002 161° C. |
| 19 | 4-CF₃ | 2-Cl | OC₄H₉(i) | b.p.·0.03 173° C. |
| 20 | 4-CF₃ | 2-Cl | NHCH₃ | m.p. 107-110° C. |
| 21 | 4-CF₃ | 2-Br | OC₂H₅ | b.p.·0.04 163° C. |
| 22 | 4-CF₃ | H | O—cyclohexyl | b.p.·0.1 180° C. |
| 23 | 4-CF₃ | 2-Cl | O—cyclohexyl | b.p.·0.06 189° C. |
| 24 | 4-CF₃ | H | OC₆H₅ | m.p. 38-43° C. |
| 25 | 4-CF₃ | 2-Cl | OC₆H₅ | b.p.·0.01 200° C. |
| 26 | 4-CF₃ | H | SC₆H₅ | m.p. 57-59° C. |
| 27 | 4-CF₃ | 2-Cl | SC₆H₅ | m.p. 45-48° C. |
| 28 | 4-CF₃ | H | NH₂ | m.p. 156-157° C. |
| 29 | 4-CF₃ | H | NH—NH₂ | m.p. 127-135° C. |
| 30 | 4-CF₃ | 2-Cl | NH₂ | m.p. 96-98° C. |
| 31 | 4-CF₃ | 2-Cl | NH—NH₂ | m.p. 147-149° C. |

EXAMPLE 32

α-[4-(4'-trifluoromethyl-phenoxy)-phenoxy]-propionic acid anilide (a) 35 g (0.106 mole) of the carboxylic acid as obtained in Example 2, 35 g of thionyl chloride and one drop of dimethyl formamide were refluxed for 3 hours and the excess thionyl chloride was distilled off under reduced pressure. After distillation 32.8 g (90% of theory) of α-[4-(4'-trifluoromethyl-phenoxy)-phenoxy]-propionic acid chloride boiling at 140° C. under 0.01 Hg were obtained.

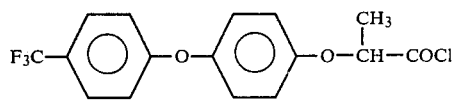

(b) 32 g (0.09 mole) of the acid chloride were dissolved in 50 ml toluene and the solution was added to a solution of 16.8 g (0.18 mole) aniline in 100 ml toluene. The mixture was stirred for one hour, filtered with suction and the precipitate dispersed in 100 ml 1 N HCl. The mixture was suction-filtered, the precipitate washed with water and the reaction product was recrystallized from ethanol. 25.4 g (70% of theory) α-[4-(4'-trifluoromethyl-phenoxy)-phenoxy]-propionic acid anilide melting at 134° C. were obtained.

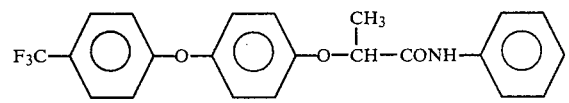

The following compounds of formula I were prepared in analogous manner:

| Example No. | R¹ | R² | melting point °C. |
|---|---|---|---|
| 33 | Cl | NH—⟨phenyl⟩ | 127 |
| 34 | Cl | NH—⟨phenyl⟩—Cl | 137-138 |
| 35 | H | NH—⟨phenyl⟩ | 134 |
| 36 | H | NH—⟨phenyl⟩—CH₃ | 123-124 |
| 37 | H | NH—⟨phenyl⟩—Cl | 142-144 |
| 38 | H | NH—⟨phenyl with CF₃⟩ | 125-127 |
| 39 | H | NH—⟨phenyl⟩—Cl (with Cl) | 123-124 |
| 40 | Cl | NH—⟨phenyl⟩—CH₃ | 139-142 |
| 41 | Cl | NH—⟨phenyl with CF₃⟩ | 107-108 |
| 42 | Cl | NH—⟨phenyl⟩—Cl (with Cl) | 121-126 |

In the following biological tests the following compounds indicated by their generic names were used:

Dichloroprop = 2-(2,4)-dichlorophenoxypropionic acid,

Chlorophenpropmethyl = 2-chloro-3(4-chlorophenyl)-methyl-propionate,

Nitralin = N,N-dipropyl-2,6-dinitro-4-methylsulfonyl aniline,

Triallate=N,N-diisopropyl-thiol-2,3,3-trichloroallyl carbamate.

EXAMPLES OF APPLICATION

EXAMPLE I

Seeds of weeds of different botanic families were sown in pots and covered with soil. On the same day the soil was sprayed with wettable formulations suspended in water and containing as active substance the compound of Example 1. As comparative agent Dichloroprop was used in the same manner.

In a further test the wettable powder formulations were sprayed on plants in the 2 to 3 leaf stage.

The results (and also the results of all following tables) were evaluated according to the following scheme in degree of damage in percent:

| number | weeds | crop plants |
|---|---|---|
| 1 | 100 | 0 |
| 2 | 97.5 to 100 | 0 to 2.5 |
| 3 | 95 to 97.5 | 2.5 to 5 |
| 4 | 90 to 95 | 5 to 10 |
| 5 | 85 to 90 | 10 to 15 |
| 6 | 75 to 85 | 15 to 25 |
| 7 | 65 to 75 | 25 to 35 |
| 8 | 32.5 to 65 | 35 to 67.5 |
| 9 | 0 to 32.5 | 67.5 to 100 |

In this scheme number 4 is still considered an acceptable herbicidal effect in weeds and satisfactory preserving effect on crop plants (cf. Bolle Nachrichtenblatt des Deutschen Pflanzenschutzdienstes 16. 1964, pages 92–94).

The results of the following Table I show, that, in contrast to Dichloroprop, the compound of the invention has a negligible effect against broad leaf weeds, even if used in a high dosage of 2.5 kg of active substance per hectare. Its special effect was restricted to species of the family of Graminacea, represented by Lolium, Alopecurus and Echinochloa, against which, as well as against other grasses, Dichloroprop was ineffective.

EXAMPLE II

Seeds of sugar beet, rape, foxtail grass (*Alopecurus myosuroides*) and wild oat (*Avena fatua*) were sown in pots and brought to germination in the greenhouse. When the plants had developed 3–4 leaves they were sprayed with aqueous suspensions of the compounds of the invention. As comparative agent chlorphenpropmethyl was used.

The result indicated in Table II shows that 4 weeks after the treatment the important weeds foxtail grass and wild oat had been substantially destroyed by the compounds of Examples 1 and 3 in a concentration of 0.31–0.62 kg/hectare, while the crop plants were not damaged. Chlorphenpropmethyl required a much higher concentration (1.25–2.5 kg/hectare) to control wild oat and did no harm to foxtail grass.

TABLE I

Effect on broad-leaf weeds and weed grasses; tests in pots in the greenhouse, dosage 2.5 kg of active compound per hectare

| | pre-emergence treatment | | post-emergence treatment | |
|---|---|---|---|---|
| types of weeds | compound of Ex. 1 | Dichloroprop | compound of Ex. 1 | Dichloroprop |
| A. broad-leaf weeds (dicotyledons) | | | | |
| Galium | 9 | 2 | 9 | 2 |
| Matricaria | 8 | 5 | 9 | 4 |
| Ipomoea | 9 | 2 | 9 | 3 |
| Sinapsis | 9 | 2 | 8 | 1 |
| Amaranthus | 5 | 1 | 7 | 1 |
| B. weed grasses (monocotyledons) | | | | |
| Lolium | 1 | 9 | 1 | 9 |
| Alopecurus | 1 | 9 | 1 | 9 |
| Echinochloa | 1 | 9 | 1 | 9 |

Dichloroprop = 2-(2',4'-dichlorophenoxy)-propionic acid

TABLE II

Test in pots in the greenhouse, treatment after germination, dosage in kg of active compound per hectare

| | Chlorphenpropmethyl | | | compound of Ex. 1 | | | compound of Ex. 3 | | |
|---|---|---|---|---|---|---|---|---|---|
| types of plants | 2.5 | 1.25 | 0.62 | 1.25 | 0.62 | 0.31 | 1.25 | 0.62 | 0.31 |
| A. weed grasses | | | | | | | | | |
| *Alopecurus myosuroides* | 9 | 9 | 9 | 2 | 5 | 9 | 1 | 2 | 2 |
| *Avena fatua* | 1 | 4 | 8 | 2 | 4 | 8 | 1 | 3 | 4 |
| B. crops | | | | | | | | | |
| sugar beet | 1 | 1 | 1 | 1 | 1 | 1 | 1 | 1 | 1 |
| rape | 1 | 1 | 1 | 1 | 1 | 1 | 1 | 1 | 1 |

EXAMPLE III

Seeds of various weed grasses and crop plants were sown in pots and caused to germinate in a greenhouse. When the plants had developed 3–4 leaves they were sprayed with aqueous suspensions of compounds of the invention. The test results, 4 weeks after the treatment, are indicated in Table III.

The results of Table III show that the compounds of the invention efficiently combat a number of important weed grasses without damaging crop plants such as cotton, soy bean and peanut. It is to be noted that maize is also destroyed. Maize (which is generally a crop plant) is considered a weed in large areas of the United States when soybeans are grown after maize. An effective method of controlling maize in soybean cultures was not known until now.

The following other types were also treated with the same concentrations of active compound and remained undamaged: sugar beet, fodder beet, spinach, cucumber, muskmelon, water melon, purple clover, lucerne, dwarf bean, pea, horse bean, flax, carrot, celery, rape, cabbage, tomato, tobacco, potato. This shows that the compounds of the invention can be used in dicotyledonous crops even in high concentration without risk.

TABLE III

Test in pots in the greenhouse, treatment after emergence
dosage in kg of active compound per hectare

| types of plants | | compound of Ex. 1 0.62 | compound of Ex. 3 1.25 |
|---|---|---|---|
| A | weed grasses | | |
| | Zea mays | 2 | 1 |
| | Setaria viridis | 1 | 1 |
| | Setaria lutenscens | 1 | 1 |
| | Echinochloa crus-galli | 1 | 1 |
| | Eleusine indica | 1 | 1 |
| | Digitaria sanguinalis | 3 | 1 |
| | Leptochloa dubia | 1 | 2 |
| | Panicum dichotomiflorum | 1 | 1 |
| | Lolium multiflorum | 2 | 4 |
| B | crop plants | | |
| | cotton | 1 | 1 |
| | peanut | 1 | 1 |
| | soybean | 1 | 1 |

The compounds of Examples 2, 4–11, 22, 24 and 26 had an effect similar to that of the compound of Example 1 while the compounds of Examples 13–19, 21, 23, 25 and 29 had the same efficiency as the compound of Example 3.

EXAMPLE IV

Perennial weed grasses play an important part in agriculture and generally are difficult to combat. The following test shows that such weeds can be efficiently controlled with the compounds of the invention.

Rhizomes of couch grass (*Agropyron repens*) and Bermuda grass (*Cynodon dactylon*) were placed in pots and in the greenhouse the plants were allowed to develop for 4 weeks.

On some pots the above-ground parts of the plants were cut off and on the same day the surface of the soil or the leaves were sprayed with aqueous suspensions of the compounds of the invention. The result is indicated in Table IV. It can be seen that the compounds of the invention were very effective against couch grass and Bermuda grass.

EXAMPLE V

In many rice cultivating countries chickweed (*Echinocloa crus-galli*) is one of the most important weeds. The following test demonstrates that chickweed can be controlled in rice by the compounds of the invention.

Rice plants in the 3 to 4 leaf stage were transferred into pots having a closed bottom so that they could be watered with a water level 1 cm above soil surface. After the transfer chickweed was sown in the pots and when the weed started to germinate the pots were flooded. At the same day, the compounds of the invention were added to the standing water and the water was slightly stirred. This method of treatment can be compared with the application of granules in practice where the granules are spread into the standing water. 4 weeks after treatment it could be seen that the compounds of the invention had an excellent effect on the weed and did no harm to the rice. The results are indicated in Table V.

EXAMPLE VI

Seeds of various weed grasses and crop plants were sown in pots and on the day sowing aqueous suspensions of compounds of the invention were sprayed on the surface of the soil. Nitralin and Triallate were used as comparative substances.

The result indicated in Table VI shows that the compounds of the invention had an excellent effect on the weed grasses. The comparative herbicides were also effective to some extent but they did not cover the broad spectrum controlled by the compounds of the invention. The compounds of the invention did no harm to the following crop plants: sugar beet, spinach, cucumber, lucerne, purple clover, flax, cotton, carrot, sunflower, rape, peanut, soybean, dwarf bean, pea, horse bean, which had been sown on the same day. Plants of cabbage, tomato and tobacco which were planted into the soil treated with the compounds also showed no damage.

The result shows that the compounds of the invention can be used in the pre-emergence process in a large number of crops and that they control a wide spectrum of weed grasses. Comparative, well known herbicides can also be used, but they do not cover the broad spectrum of the compounds of the invention.

TABLE IV

Test in pots in the greenhouse with perennating grasses
dosage 2.5 kg of active compound per hectare

| | | leaf treatment with | |
|---|---|---|---|
| type of plant | soil treatment with compound of Ex. 1 | compound of Ex. 1 | compound of Ex. 3 |
| *Agropyron repens* | 1 | 3 | 2 |
| *Cynodon dactylon* | 1 | 4 | 2 |

TABLE V

Test in flooded pots in the greenhouse
dosage in kg of active compound per hectare

| | compound according to Example | |
|---|---|---|
| | (1) | (3) |
| types of plants | 0.62 | 0.31 |
| *Echinochloa crus-galli* | 2 | 1 |
| rice (transplanted) | 1 | 1 |

TABLE VI

Test in pots in the greenhouse, treatment prior to emergence
dosage in kg of active compond per hectare

| | compound of Example | | | |
|---|---|---|---|---|
| Types of plants | (1) 1.25 | (3) 1.25 | Nitralin 1.25 | Triallate 1.25 |
| weed grasses | | | | |
| Avena | 3 | 4 | 6 | 2 |
| Alopecurus | 1 | 1 | 4 | 1 |
| Poa | 1 | 2 | 1 | 6 |
| Echinochloa | 1 | 1 | 2 | 7 |
| Setaria | 1 | 1 | 6 | 8 |
| Lolium | 1 | 1 | 2 | 6 |

We claim:

1. Compounds of the formula I

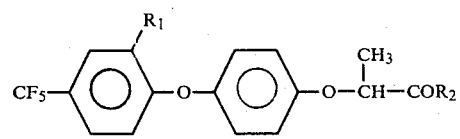

in which
R$_1$ is hydrogen or halogen, and
R$_2$ is hydroxy, (C$_1$-C$_6$)alkoxy, cyclohexyloxy, phenyloxy, or the group -Ocat werein cat stands for the cation of an inorganic or organic base.

2. A compound as claimed in claim 1 which is

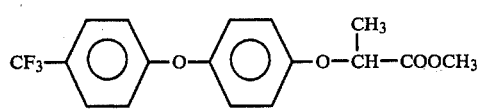

3. A compound as claimed in claim 1 which is

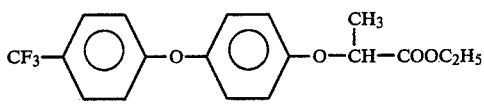

4. A compound as claimed in claim 1 which is

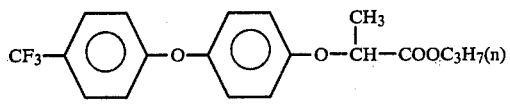

5. A compound assclaimed in claim 1 which is

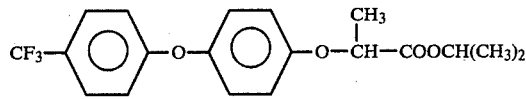

6. A compound as claimed in claim 1 which is

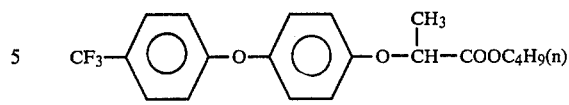

7. A compound as claimed in claim 1 which is

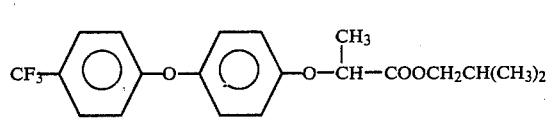

8. A compound of the formula

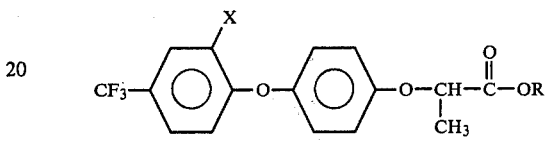

wherein
R is phenyl, and
X is hydrogen or halogen.

9. Herbicidal composition containing as active substance a compound of claim 1 in combination with the conventional inert component.

10. Method of combating weeds in crop plants which comprises treating the cultivated area with an effective amount of a compound as claimed in claim 1.

* * * * *